United States Patent [19]

Ueda

[11] Patent Number: 4,788,967
[45] Date of Patent: Dec. 6, 1988

[54] ENDOSCOPE

[75] Inventor: Yasuhiro Ueda, Tokyo, Japan

[73] Assignee: Olympus Optical Co., Ltd., Japan

[21] Appl. No.: 927,082

[22] Filed: Nov. 5, 1986

[30] Foreign Application Priority Data

Nov. 13, 1985 [JP] Japan .................. 60-254109

[51] Int. Cl.⁴ .................................. A61B 1/06
[52] U.S. Cl. .................................. 128/6; 128/4; 350/96.26
[58] Field of Search .................. 128/4–6; 350/96.23, 96.24, 96.25, 96.26; 354/62, 63; 358/98, 229, 100

[56] References Cited

U.S. PATENT DOCUMENTS

| 4,350,150 | 9/1982 | Kubota et al. | 128/6 |
| 4,367,729 | 1/1983 | Ogiu | 128/6 |
| 4,419,987 | 12/1983 | Ogiu | 128/6 |
| 4,576,145 | 3/1986 | Tsuno . | |

FOREIGN PATENT DOCUMENTS 53-111591 6/1978 Japan .
60-249114 9/1985 Japan .

Primary Examiner—Barry S. Richman
Assistant Examiner—T. J. Wallen

[57] ABSTRACT

An endoscope includes an operating section and an insertion section extending from the operating section. The insertion section has a flexible tube formed of a flexible synthetic resin and having a plurality of insertion channels extending in the axial direction of the flexible tube. A rigid member is attached to the distal end of the tube. The rigid member has through holes communicating with the channels, respectively. An objective optical system is arranged in one of the through holes. An image guide fiber is passed through one of the insertion channels, and its distal end portion is inserted fixedly in the through hole and optically connected to the objective optical system.

6 Claims, 3 Drawing Sheets

1

ENDOSCOPE

BACKGROUND OF THE INVENTION

The present invention relates to an endoscope, and more specifically to an endoscope having an insertion section formed of a multi-lumen tube.

Recently, in order to make the insertion section small in diameter, there have been endoscopes developed whose insertion section is formed of a multi-lumen tube, which has a small diameter. The multi-lumen tube includes a solid tube member of flexible resin, having a plurality of insertion channels extending in its axial direction. The tube member serves directly as the insertion section. An image guide fiber, light guide fiber, etc., are inserted individually in the channels.

In general, an objective optical system and an illuminating optical system are disposed in the distal end portion of the insertion section. Since the insertion section, formed of the multi-lumen tube, is flexible, its distal end portion can be deformed by the load of the optical systems therein. Accordingly, the optical systems may possibly become eccentric to the image guide fiber or light guide fiber, or their optical axes may incline at some angle to the central axis of the image or light guide fiber. In such cases, the optical systems cannot function well.

Moreover, resin is exposed from the distal end portion of the insertion section. Therefore, if a laser probe is passed through one of the channels, and if a laser beam is radiated from the distal end of the insertion section, the distal end portion will be burned by the laser beam reflected by an irradiated region of a subject's body.

SUMMARY OF THE INVENTION

The present invention has been contrived in consideration of these circumstances, and is intended to provide an endoscope, in which optical systems can fulfill their functions satisfactorily, and in which an insertion section can be prevented from being damaged when a laser beam is applied to the affected part of a patient's body.

In order to achieve the above object, according to an endoscope of the present invention, a rigid portion is attached to the distal end of an insertion section. The rigid portion has at least one through hole, which communicates with one of the channels of the insertion section. An optical system is disposed in the through hole, and the distal end of an image guide, passed through the channel, is inserted in the through hole and connected optically to the optical system.

BRIEF DESCRIPTION OF THE DRAWINGS

FIGS. 1 to 4 show an endoscope according to a first embodiment of the present invention, in which FIG. 1 is a side view of the endoscope, FIG. 2 is a sectional view of the distal end portion of an insertion section, and FIGS. 3 and 4 are sectional views taken along lines III—III and IV—IV of FIG. 2, respectively.

DETAILED DESCRIPTION OF THE PREFERRED EMBODIMENTS

Preferred embodiments of the present invention will now be described in detail with reference to the accompanying drawings.

Figure 1:
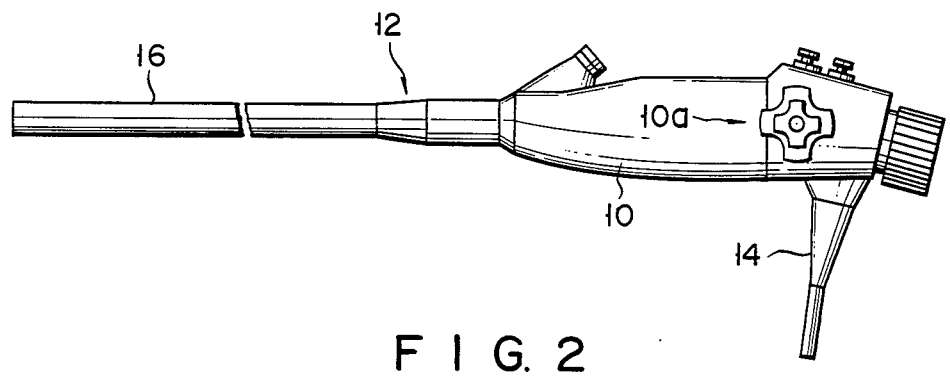

FIG. 1 shows an outline of an endoscope according to the present invention. The endoscope comprises operating section 10, insertion section 12, and universal cord 14. Section 12 and cord 14 both extend from section 10.

Figure 2:
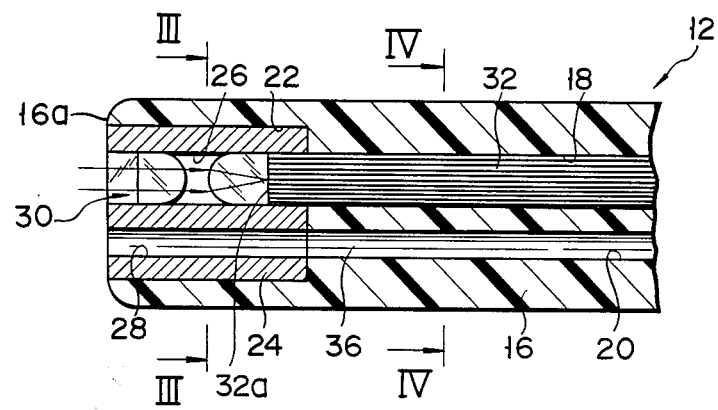
Figure 3:
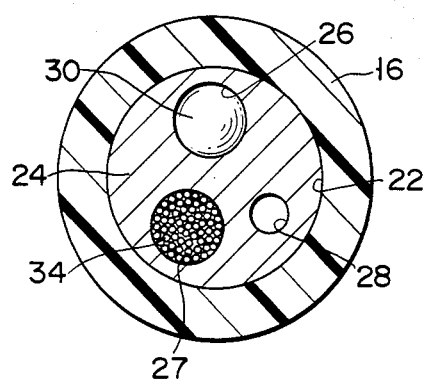
Figure 4:
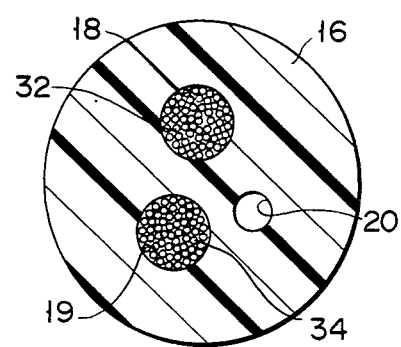

As shown in FIGS. 2 to 4, insertion section 12 is composed of flexible tube 16, made of synthetic resin, such as polyurethane resin or ethylene tetrafluoride resin. Tube 16 has three insertion channels 18, 19 and 20 extending in its axial direction, and distal end face 16a. End face 16a is formed with recess 22, having a circular cross section, and channels 18, 19 and 20 open to the bottom surface of the recess. Fitted in recess 22 is cylindrical rigid member 24 which, made of stainless steel, has a diameter and length equivalent to those of the recess. Member 24 is removably fixed to tube 16 by means of a bonding agent. Member 24 has three through holes 26, 27 and 28 bored through it, in its axial direction. These holes have positions and diameters corresponding to those of channels 18, 19 and 20 of flexible tube 16. Thus, when member 24 is fixed to tube 16, holes 26, 27 and 28 communicate coaxially with bores 18, 19 and 20, respectively. Rigid member 24 is not limited to metal in material, and may alternatively be formed of ceramic material, such as alumina and zirconia, or be formed from carbon, or rigid plastic material, such as polysulfone resin, polycarbonate, denaturalized polyphenylene oxide, etc.

Objective optical system 30 and an illuminating optical system (not shown) are provided in holes 26 and 27, respectively, of rigid member 24. Image guide fiber 32 is passed through channel 18 of flexible tube 16. The distal end portion or incidence-side end portion of fiber 32 is inserted in hole 26 of member 24, so as to be fixed to member 24 and connected optically to optical system 30. Thus, fiber 32 is kept in alignment with the optical axis of system 30. The distal end portion of fiber 32 has an end face 32a and is fixed to member 24 so that an optical image is imaged on the end face by optical system 30. The proximal end portion of fiber 32 extends up to operating section 10. Light guide fiber 34 is passed through channel 19. The distal end portion of fiber 34 is inserted in hole 27 of rigid member 24, so as to be fixed to member 24 and connected optically to the illuminating system. Thus, fiber 34 is kept in alignment with the optical axis of the illuminating system. The proximal end portion of fiber 34 extends through operating section 10 and universal cord 14. Channel 20 and hole 28 define instrument channel 36, into which a forceps, laser probe, or some other medical instrument is to be inserted.

According to the endoscope constructed in this manner, rigid member 24 is attached to the distal end of flexible tube 16, and objective optical system 30 and the illuminating optical system are arranged within member 24. The respective distal end portions of image guide fiber 32 and light guide fiber 34 are fixed to rigid member 24 so that their optical axes are in alignment with their corresponding optical systems. Even when flexible tube 16 undergoes elastic deformation, therefore, the optical systems cannot become eccentric to guide fibers 32 and 34, that is, the optical axes of the optical systems cannot be deviated from those of the fibers. Thus, both the optical systems can fulfill their functions satisfactorily.

A laser probe is passed through instrument channel 36, to cauterize the affected part, with its distal end portion projected from the distal end of flexible tube 16. In doing this, the distal end portion of tube 16 is subjected to a laser beam reflected by the affected part. According to this embodiment, however, rigid member 24 is fixed to the distal end of tube 16, so that the synthetic resin, constituting the tube, cannot receive the laser beam directly. Thus, the distal end of the flexible tube, or the distal end portion of insertion section 12, can be prevented from being damaged by the beam.

Moreover, rigid member 24 is removably fixed to flexible tube 16. Therefore, in repairing insertion section 12, if its image guide fiber is broken, for example, the rigid member, along with the optical systems, can be removed from the flexible tube. Thus, only a damaged portion or portions of the insertion section can be repaired or replaced, so that the optical systems can be reused.

In the embodiment described above, furthermore, rigid member 24 is bonded fixedly to flexible tube 16. Alternatively, however, it may be fixed by press fit or ultrasonic welding.

Figure 5:
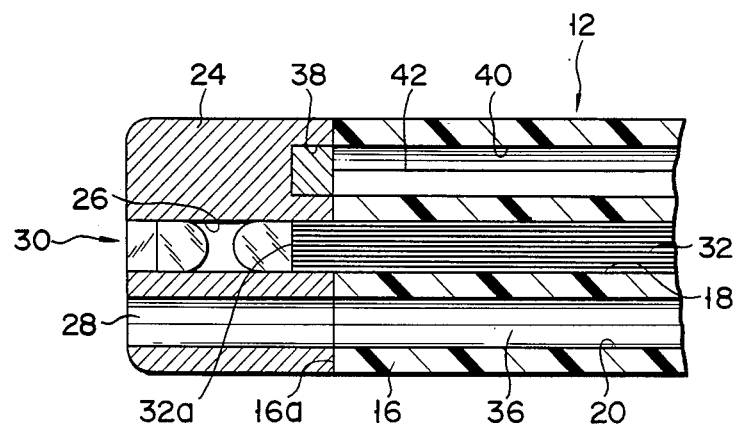
FIGS. 5 to 8 are sectional views of the distal end portions of insertion sections of endoscopes according to second to fifth embodiments of the invention, respectively.

FIG. 5 shows the distal end portion of an insertion section of an endoscope according to a second embodiment of the present invention. According to this embodiment, rigid member 24 is in the form of a cylinder, having the same diameter as flexible tube 16, and is bonded fixedly to distal end face 16a of tube 16. Member 24 has recess 38 in its end face on the flexible-tube side, besides through holes 26, 27 and 28. Also, tube 16 is formed with channel 40, communicating with recess 38, besides channel 18, 19 and 20. Operating wire 42 for bending insertion section 12 is passed through channel 40. The distal end of wire 42 is fixed to recess 38 of rigid member 24 by brazing or the like. The proximal end of wire 42 is connected to operating knob 10a (FIG. 1), which is attached to operating section 10. With respect to other components, the second embodiment is constructed in the same manner as the first embodiment, so that a description of those components is omitted herein. Thus, the second embodiment can provide the same effects as the first embodiment.

Figure 6:
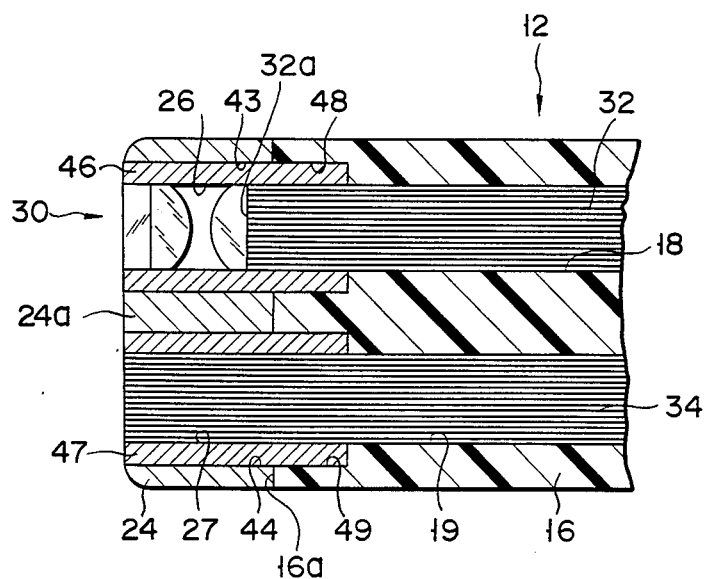

According to a third embodiment shown in FIG. 6, rigid member 24 has cylindrical body 24a, which has substantially the same diameter as flexible tube 16, and is bonded fixedly to distal end face 16a of tube 16. Body 24a is formed with bores 43 and 44, extending in its axial direction. Member 24 includes fixed cylinders 46 and 47, which are inserted fixedly in their corresponding bores of body 24a. One-side end portions of cylinders 46 and 47 project from body 24a toward flexible tube 16, and are press-fitted into hollows 48 and 49, respectively, formed in end face 16a of tube 16. The inner peripheral surface of cylinder 46 defines hole 26, which communicates with channel 18. Likewise, the inner peripheral surface of cylinder 47 defines hole 27, which communicates with channel 19. Objective optical system 30 is disposed in hole 26. Also, the distal end portion of image guide fiber 32 is fixed in hole 26. In the third embodiment, no illuminating optical system is used, and the distal end portion of light guide fiber 34 is inerted fully in hole 27, thus reaching the distal end of rigid member 24.

Constructed in this manner, the third embodiment provides the following effect, besides the same effects of the first embodiments. In the third embodiment, body 24a of rigid member 24 is bonded to distal end face 16a of flexible tube 16, and the respective end portions of fixed cylinders 46 and 47 are press-fitted individually into the distal end portion of tube 16. Thus, the strength of fixation of member 24 to tube 16 is improved.

Figure 7:
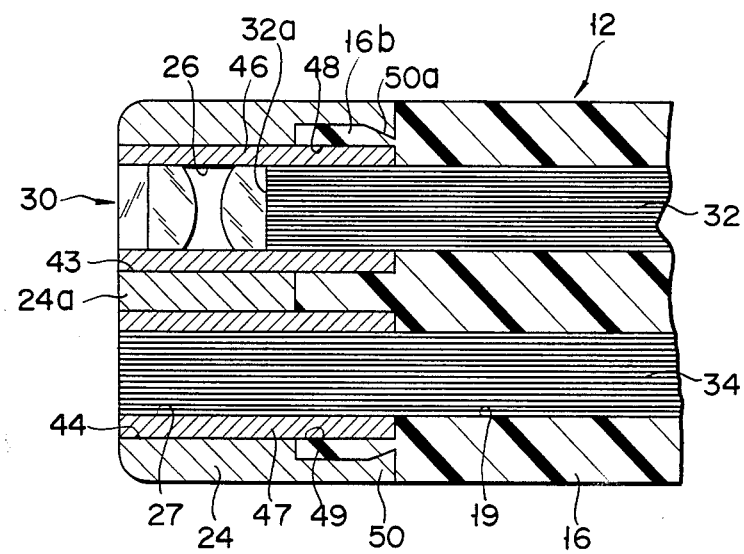

FIG. 7 shows a fourth embodiment of the present invention. This embodiment is constructed substantially in the same manner as the third embodiment, provided body 24a of rigid member 24 includes ring-shaped projection 50, which protrudes from the outer peripheral edge of body 24a, on the distal-end side of flexible tube 16, toward tube 16. Projection 50 has fixing claw 50a which protrudes inward from the inner peripheral surface of its projecting end. The distal end portion of tube 16 has a smaller diameter than any other portions thereof, thus constituting small-diameter portion 16b. Projection 50 is fitted on portion 16b so that claw 50a bites into the outer peripheral surface of portion 16b.

According to the fourth embodiment constructed in this manner, the strength of fixation of rigid member 24 to flexible tube 16 is improved further.

Figure 8:
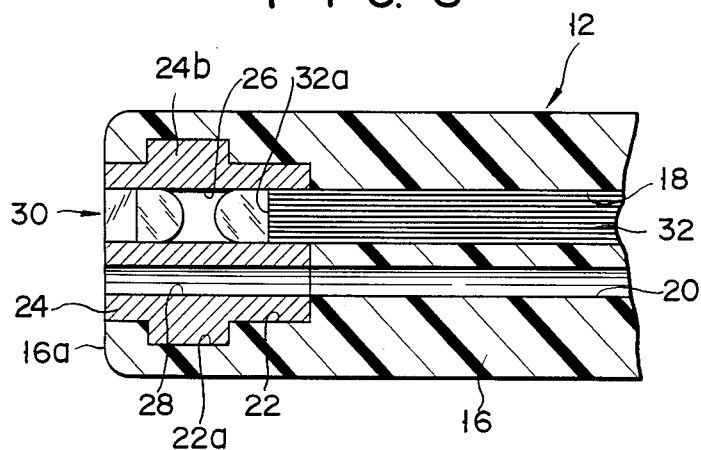

A fifth embodiment of the present invention is shown in FIG. 8. This embodiment differs from the first embodiment only in the following points. Cylindrical rigid member 24 has ring-shaped projection 24b on its outer peripheral surface, and annular groove 22a is formed, correspondingly, on the wall surface of recess 22, in the distal end portion of flexible tube 16. Member 22 is bonded to recess 22 so that projection 24b is press-fitted into groove 22a of recess 22.

According to the fifth embodiment constructed in this manner, the strength of fixation of rigid member 24 to flexible tube 16 is greater than in the case of the first embodiment.

What is claimed is:
1. An endoscope comprising:
    an operating section;
    an insertion section extending from the operating section and adapted to be inserted into a body cavity, said insertion section including a bendable tube, formed of a bendable synthetic resin, and having a distal end face, a recess formed in the distal end face, and a plurality of insertion channels extending in an axial direction of the tube and opening to a bottom surface of the recess;
    a non-bendable portion including a non-bendable member which corresponds in shape to the recess and fitted in the recess, the member having at least one through hole, communicating with one of the channels of the insertion section;
    an objective optical system arranged in the through hole of the non-bendable portion; and
    an image guide fiber inserted in the channel communicating with the through hole, said fiber having a distal end portion inserted fixedly in the through hole and connected optically to the objective optical system.

2. The endoscope according to claim 1, wherein said recess has an engaging groove on an inner peripheral surface thereof, and said non-bendable member has a projection, press-fitted in the groove.

3. The endoscope according to claim 1, wherein said non-bendable portion has a second through hole communicating with another insertion channel of the flexible tube and defining an instrument insertion channel, in conjunction with the second through hole, and a third through hole communicating with still another insertion channel, and which further comprises a light guide fiber inserted in the third through hole, said light guide fiber having a distal end portion inserted fixedly in the third through hole.

4. The endoscope according to claim 1, wherein said non-bendable portion is formed of a ceramic material selected from the group of materials consisting of alumina and zirconia.

5. The endoscope according to claim 1, wherein said non-bendable portion is formed of a rigid plastic material, selected from the group of materials consisting of polysulfone resin, polycarbonate, and denaturalized polyphenylene oxide.

6. The endoscope according to claim 1, wherein said non-bendable portion is formed of carbon.

* * * * *